United States Patent [19]

Walter

[11] 4,058,560
[45] Nov. 15, 1977

[54] CHEMICAL PROCESS
[75] Inventor: Thomas J. Walter, Baton Rouge, La.
[73] Assignee: Ethyl Corporation, Richmond, Va.
[21] Appl. No.: 718,954
[22] Filed: Aug. 30, 1976
[51] Int. Cl.² .............................................. C07C 59/22
[52] U.S. Cl. ................................................. 260/535 P
[58] Field of Search ..................................... 260/535 P
[56] References Cited
U.S. PATENT DOCUMENTS
3,821,296  6/1974  Blumbergs et al. .............. 260/535 P

*Primary Examiner*—Paul J. Killos
*Attorney, Agent, or Firm*—Donald L. Johnson; John F. Sieberth; Shelton B. McAnelly

[57] ABSTRACT

It is disclosed that the production and recovery of water soluble carboxymethyloxy succinic acid salt from zinc or alkaline earth metal carboxymethyloxy succinic acid salt is enhanced by adding the zinc or alkaline earth metal salt to a carbonate which forms therewith a water soluble carboxymethyloxy succinic acid salt. The treating process, performed in an aqueous system, produces a zinc or alkaline earth metal carbonate precipitiate which is readily and quickly filtered providing a significant improvement in filterability over that experienced when the starting carbonate is added to the alkaline earth metal carboxymethyloxy succinate. Preferably the addition is progressive; that is, the zinc or alkaline earth metal carboxymethyloxy succinate is added to the carbonate gradually so that for the most part the carbonate is present in excess over the other reactant.

9 Claims, No Drawings

CHEMICAL PROCESS

BACKGROUND OF THE INVENTION

1. Field of the Invention

This invention relates to the preparation of alkali metal and other water soluble salts of carboxymethyloxy succinic acid from maleic acid and glycolic acid.

2. Description of the Prior Art

Carboxymethyloxy succinic acid and its water soluble salts have utility as builders as disclosed in U.S. Pat. No. 3,914,297 which also discloses a preferred method of preparing such materials by reacting maleic acid and glycolic acid in the presence of zinc or alkaline earth metal ions to form zinc or alkaline earth metal salt of carboxymethyloxy succinic acid and then treating such zinc or alkaline earth metal salt to convert it into the desired water soluble salt. Typically, in the treating operation as performed in the prior art sodium carbonate is added to the zinc or alkaline earth metal salt to produce trisodium carboxymethyloxy succinate and by-product zinc or alkaline earth metal carbonate, the latter in the form of a precipitate which must be removed to provide a solution from which the trisodium carboxymethyloxy succinate can be recovered. Unfortunately the removal of the by-product carbonate salt is very difficult when attempted as described in the process of U.S. Pat. No. 3,914,297. Alleviation of the difficulty is sought as described in U.S. Pat. No. 3,821,296 which uses a "heel" of trisodium carboxymethyloxy succinate in the reaction of calcium carboxymethyloxy succinate and sodium carbonate. It would be desirable to provide a suitable treating process which does not require the use of a "heel."

SUMMARY OF THE INVENTION

It has been discovered that the difficult filtration problem connected with the removal of zinc or alkaline earth metal carbonate from water soluble carboxymethyloxy succinate is alleviated to a considerable extent by performing the treating step of the process in such a way that the zinc or alkaline earth metal carboxymethyloxy succinate solution is added to the carbonate cation source material rather than in the opposite order as taught in U.S. Pat. No. 3,914,297. Thus, for example, in accordance with the teachings of the present invention a zinc or alkaline earth metal carboxymethyloxy succinate system preferably obtained from the reaction of maleic acid and glycolic acid in the presence of zinc or alkaline earth metal ions is added gradually to a suitable alkali metal, ammonium, morpholinium, alkyl ammonium, mono-, di- or trialkanol ammonium or equivalent carbonate cation source material. With this method of combination of the reactants, excellent filtration rates are obtained without the complication of handling the "heel" material third feed stream.

Preferred carbonate materials are the alkali metal carbonates whose cations are set forth in Group 1A of the 1955 Periodic Table of Fisher Scientific Company, preferably sodium carbonate or potassium carbonate, especially the former. Preferred cations present at the reaction of maleic acid and glycolic acid and hence present in the zinc or alkaline earth metal carboxymethyloxy succinate treated are alkaline earth metal cations as set forth in the foregoing periodic table, preferably calcium or magnesium, especially the former.

The carbonate by-product that results from the treating processing in accordance with the present invention is suitable for recycle to the reaction of maleic acid and glycolic acid to provide at least a portion of the zinc or alkaline earth metal ions desired for that reaction. The water soluble carboxymethyloxy succinate solution that is obtained from the treating step is processed in any suitable manner for the recovery of the carboxymethyloxy succinic acid salt which may be recovered therefrom by evaporation of water or by salting out precipitation in the presence of a lower alkanol such as methanol. In general, methanol precipitation is preferred because it minimizes energy costs in the evaporation of water and because of the excellence of the product.

The teachings of the present invention may be utilized in numerous systems in addition to those of the preferred calcium and sodium systems. Typical materials produced in accordance with the process are trisodium carboxymethyloxy succinate, tripotassium carboxymethyloxy succinate, trilithium carboxymethyloxy succinate, triammonium carboxymethyloxy succinate, the normal monoethanol amine salt of carboxymethyloxy succinic acid, the normal diethanol amine salt of carboxymethyloxy succinic acid, the normal triethanol amine salt of carboxymethyloxy succinic acid, the normal tetramethyl ammonium salt of carboxymethyloxy succinic acid, tri(ethyl ammonium) carboxymethyloxy succinate, the normal monoisopropanol amine salt of carboxymethyloxy succinic acid, the normal diisopropanol amine salt of carboxymethyloxy succinic acid, monosodium dipotassium carboxymethyloxy succinate, disodium monopotassium carboxymethyloxy succinate, the normal morpholine salt of carboxymethyloxy succinic acid, and the like. Of course, it is to be understood that the compounds of the present invention which are identified herein are available in both anhydrous and hydrated forms and that various degrees of hydration are possible with many of the compounds.

Likewise, not only are calcium ions useful in the first stage reaction of the maleic acid and glycolic acid but zinc and other alkaline earth metal ions are also useful. Such ions may be supplied in the form of any convenient compound, suitably as an oxide, hydroxide or carbonate such as calcium hydroxide, calcium carbonate, magnesium carbonate, magnesium hydroxide, zinc oxide, strontium hydroxide, or barium hydroxide.

The pH of the medium in the first stage reaction of maleic acid and glycolic acid is important and in general ranges from about 9 to about 13.0 as measured at about 25° C with pH paper manufactured by E. Merck, Darmstadt, Germany. Preferably, the pH when measured as described is from about 11.5 to about 12.8, especially from about 12.0 to about 12.3. Control of the pH can be adjusted using an oxide or hydroxide of an alkali metal or of an alkaline earth metal. For example, when recycle or fresh calcium carbonate is employed in the first stage reaction, it is generally preferred to adjust the pH with calcium hydroxide or sodium hydroxide to achieve the desired value.

The reaction of maleic acid and glycolic acid is preferably conducted at a temperature of from about 60° to about 200° C in accordance with the considerations set forth in U.S. Pat. No. 3,914,297. A preferred temperature is from about 90° to about 100° C.

The treating step when performed in accordance with the present invention with the present order of addition of reactants is preferably conducted under any suitable conditions which cause the conversion of the zinc or alkaline earth metal salt produced by the first step of the process into a water-soluble salt of the class defined which is typified herein by trisodium carboxymethyloxy succinate. Usually the treating step is performed in two phases, one an addition phase; the second, a cook phase wherein the system is gently agitated for a period of time. Treating temperature is not critical ranging from about 0° to about 100° C, typically from about 25° to about 90° C, especially from about 50° to about 75° C.

The time for the adding portion of the treating step is not especially critical and in fact any amount of time prolongation of the addition of one reactant to the other as taught herein normally will provide a distinct improvement in the filterability of the resulting calcium carbonate in comparison to that which is obtained when the alkali metal carbonate is added progressively to the zinc or alkaline earth metal carboxymethyloxy succinate solution. On the other hand, one prefers for the adding portion of the treating step to be for at least a minute and less than about 2 hours. Adding times shorter than one minute, although useful, are less desirable than somewhat longer times because it is usually less expensive to trade off more time in the treating step in order to shorten the time needed for the filtration. Adding times longer than 2 hours can be used but are rarely necessary, and hence are not generally used. Preferred adding times range from about 5 to about 75 minutes, especially from about 30 to about 60 minutes, which times are usually adequate to provide an easily filtered zinc or alkaline earth metal carbonate system which can be filtered or separated by centrifuging either in batchwise operation times ranging from about 1 to about 5 minutes or continuously.

Although the entire time for the treating step can be devoted to the addition phase, generally it is preferred to follow the addition phase with a "cook" or "soak" phase of up to about two hours duration wherein the combined reactants are agitated moderately at the same temperature as the addition phase or at a different temperature within the ranges set forth in the foregoing. Typically, one uses a "cook" temperature and time duration which are the same as the adding time and temperature.

The proportions of reactants fed in the treating operation are not especially critical; however, in general, it is preferred to use overall about stoichiometric proportions of the materials involved. Useful molar proportions of the treating carbonate to the starting zinc or alkaline earth metal carboxymethyloxy succinate range from about 0.1:1 to about 10:1; however, for the most part, especially for the first half of the addition, the carbonate source material is present in excess. It will be appreciated that the filtration time which follows the treating step is in effect a continuation or extension of the cook phase of the treating step. In some instances, this may suffice for the treating step; however, where more complete conversion of the zinc or alkaline earth metal carboxymethyloxy succinate to the water soluble carboxymethyloxy succinate is desired, it is usually preferred to employ a cook phase of duration up to about two hours and approximately equal to that of the addition phase. Such cook phase is, in effect, interposed between the addition phase and the filtration step.

Regardless of whether or not the cook phase is used, the important aspect of the present invention is the order of addition of reactants when the zinc or alkaline earth metal carboxymethyloxy succinate is combined with the carbonate source material.

The following examples indicate preferred embodiments of the present invention.

EXAMPLE I

To a 500 ml round bottom flask was added 19.6 grams of maleic anhydride, 22.1 grams of 70 percent glycolic acid in aqueous solution, 100 mls of water and 24.3 grams of lime. The pH at this point was approximately 12.1 by measured pH paper (E. Merck, range pH 11.0–13.0). The flask was then immersed in a 120° C oil bath and the contents stirred. Check by NMR was made and the reaction was stopped after the conversion of maleic acid was in excess of 90 percent. Time was approximately 2 hours but ranges from 1 to 3 hours in most cases. When the conversion was greater than 90 percent, the oil bath was removed and the reaction mixture allowed to cool to 60°. Another clean flask was charged with 35.2 grams of sodium carbonate and 20 mls of water, forming a rather thick slurry. The second flask was then immersed in an oil bath at approximately 60° C. Product from the first reaction (about 150 ml in volume) was then slowly added to the sodium carbonate slurry over a 60 minute period. This addition was performed in about 5 ml increments, spreading the 150 ml addition out over the 60 minute period. After the addition was complete, the reaction mass was stirred another 60 minutes at 60° C in a "cook" phase. Stirring the mixture during the addition of the calcium carboxymethyloxy succinate to the sodium carbonate and the subsequent "cook" phase was with moderate agitation. Vigorous agitation was not used because the calcium carbonate tends to form agglomerates which are broken up by overly vigorous agitation.

After the treating operation, the slurry of calcium carbonate and sodium CMOS was filtered using a 7 centimeter Buchner funnel and Whatman GF/A filter paper, a preferred glass type filter paper. The filtration time was measured during the filtration, noting the volume of filtrate as well as the cake thickness. Results are tabulated. Of significance are the short filtering time of 1.3 minutes, the filtration rate of 0.59 gallons per minute per square foot of filter surface, the thin filter cake which means a small amount of retained liquid and the large volume of filtrate of 120 ml.

| Example | Addition Time (Minutes) | Filtering Time (Minutes) | Filtering Rate Gallons Per Minute Per Square Foot | Cake Thickness (Inches) | Filtrate Volume (Milliliters) |
|---|---|---|---|---|---|
| I | 60 | 1.3 | 0.59 | 0.28 | 120 |
| II | 30 | 1.75 | 0.44 | 0.26 | 120 |
| III | 30 | 2.0 | 0.37 | 0.34 | 116 |
| IV | 30 | 2.0 | 0.30 | 0.31 | 94 |
| V | 5 | 4.25 | 0.16 | 0.37 | 107 |
| VI | 60 | 5.0 | 0.12 | 0.28 | 94 |
| VII | 60 | 2.0 | 0.26 | 0.37 | 82 |

-continued

| Example | Addition Time (Minutes) | Filtering Time (Minutes) | Filtering Rate Gallons Per Minute Per Square Foot | Cake Thickness (Inches) | Filtrate Volume (Milliliters) |
|---|---|---|---|---|---|
| VIII | 40 | 8.5 | 0.058 | 0.39 | 77 |
| IX | 1 | 19 | 0.028 | 0.44 | 83 |

EXAMPLES II-IV

Example I was repeated using 30 minute addition time for the treating step. Example IV apparently is anomalous in filtrate volume since its results are not in line with those of similar Examples II and III.

EXAMPLE V

Example I was repeated using 5 minute addition time.

EXAMPLE VI

Example I was repeated adding the product from the first reaction to anhydrous sodium carbonate in the second flask.

EXAMPLES VII-VIII

For comparative purposes, Example I was repeated in substantially simultaneous combination of substantially stoichiometric increments of "dry" sodium carbonate and calcium carboxymethyloxy succinate. Example VII used a 40 minute addition period while Example VIII used a 60 minute addition period. The results of Example VII especially are not bad in filtering time; however, the filtrate volumes are low and cake thickness is high showing excessive retention of filtrate in the cake. The filtrate volumes of Examples VI-IX are not directly correlated with those of Examples I-V because in Examples VI-IX the Na$_2$CO$_3$ was fed dry rather than in a slurry with 20 ml of water; however, the filtrate volume of Examples VI-IX are all less than 100 ml which is the filtrate volume of Examples I and II less 20 ml.

EXAMPLE IX

For comparative purposes, Example I was repeated with the second step treating performed with the sodium carbonate (anhydrous) added more or less all at once (over a 1 minute period) to the calcium carboxymethyloxy succinate solution from the first reaction. This is the type of treating step employed in the preferred processing of U.S. Pat. No. 3,914,297. The long filtering time, low filtering rate, thick cake and low volume of filtrate are to be compared with the overall substantially better results of foregoing Examples I-V.

I claim:

1. In the method of producing the trialkali metal salt of carboxymethyloxy succinic acid by reacting in an aqueous medium, maleic acid and glycolic acid under basic conditions in the presence of zinc or alkaline earth metal ions to produce a zinc or alkaline earth metal salt of carboxymethyloxy succinic acid and treating said zinc or alkaline earth metal salt with alkali metal carbonate thereby forming a reaction mixture containing the trialkali metal salt and zinc or alkaline earth metal carbonate, the improvement of gradually adding zinc or alkaline earth metal salt of carboxymethyloxy succinic acid to the alkali metal carbonate.

2. The process of claim 1 wherein the alkali metal carbonate is sodium carbonate.

3. The process of claim 1 wherein the zinc or alkaline earth metal salt of carboxymethyloxy succinic acid is a calcium salt.

4. The process of claim 1 wherein the maleic acid and glycolic acid are reacted in the presence of calcium ions.

5. The method according to claim 1 wherein the zinc or alkaline earth metal carbonate is separated from the alkali metal carboxymethyloxy succinate by filtering or centrifuging.

6. A process in accordance with claim 1 wherein the gradual addition is performed over a period of from about 5 minutes to about 2 hours and is followed by a cook period of from about 5 minutes to about 2 hours wherein the product of the addition is allowed to age and wherein the aged product is filtered or centrifuged to remove zinc or alkaline earth metal carbonate providing a filtrate aqueous solution of alkali metal carboxymethyloxy succinate.

7. The method according to claim 1 wherein the zinc or alkaline earth metal carbonate is separated from the aqueous solution by filtering or centrifuging and is recycled to the reaction of maleic acid and glycolic acid to provide at least a portion of the zinc or alkaline earth metal ions utilized in that reaction system.

8. The method according to claim 5 wherein the filtrate is contacted with a lower alkanol to precipitate the sodium carboxymethyloxy succinate.

9. The process of claim 8 wherein the lower alkanol is methanol.

* * * * *